Figure 1:
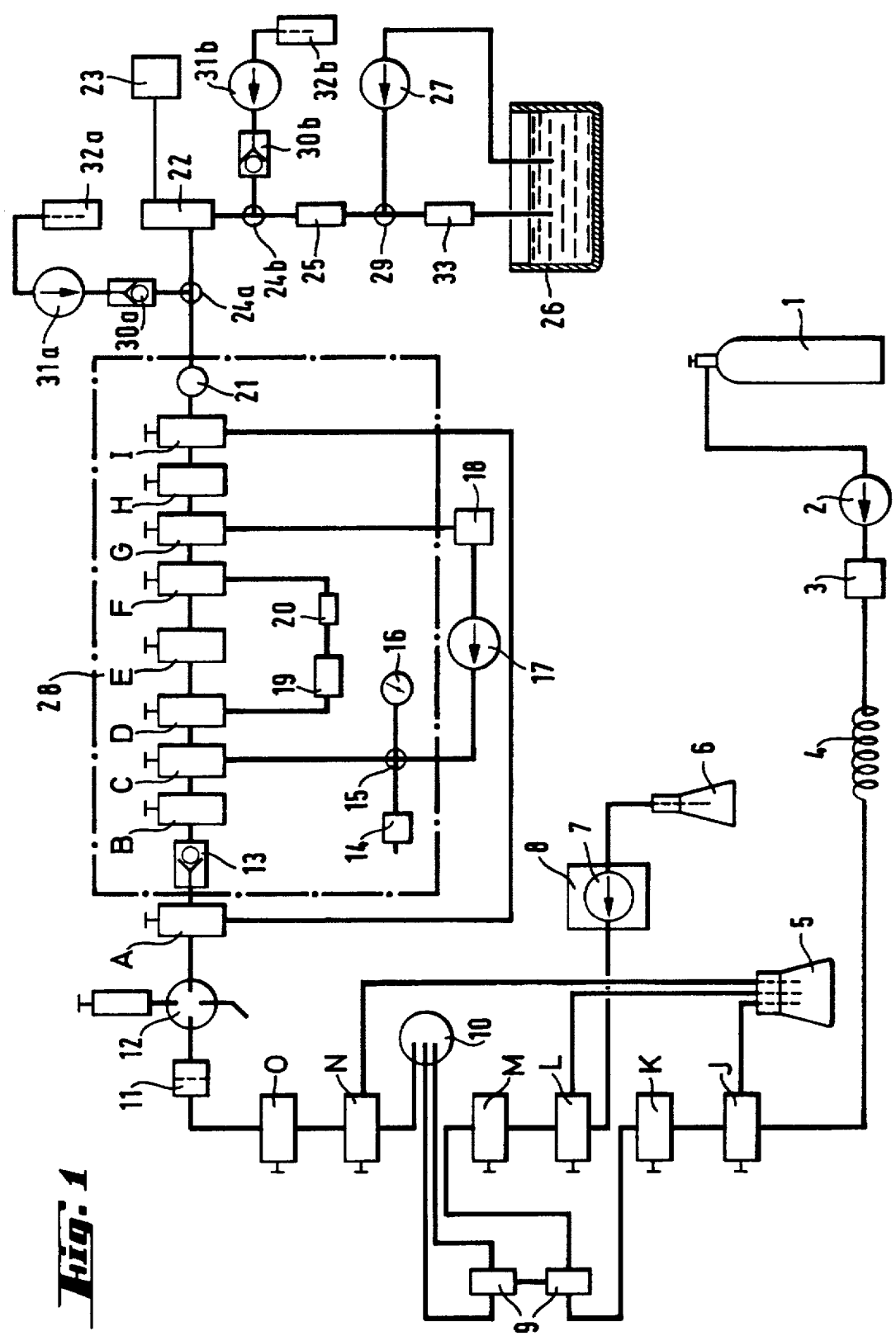

United States Patent [19]
Frederiksen et al.

[11] Patent Number: 5,700,482
[45] Date of Patent: Dec. 23, 1997

[54] PROCESS FOR THE PREPARATION OF A LIPOSOME DISPERSION UNDER ELEVATED PRESSURE CONTENTS

[75] Inventors: Lene Frederiksen; Klaus Anton, both of Basel; Peter van Hoogevest, Riehen, all of Switzerland

[73] Assignee: Ciba-Geigy Corporation, Summit, N.J.

[21] Appl. No.: 483,912

[22] Filed: Jun. 7, 1995

Related U.S. Application Data

[63] Continuation of Ser. No. 216,760, Mar. 23, 1994, abandoned.

[30] Foreign Application Priority Data

Mar. 24, 1993 [CH] Switzerland ............... 891/93

[51] Int. Cl.⁶ ............................... A61K 9/127
[52] U.S. Cl. .................. 424/450; 264/4.1; 264/4.3
[58] Field of Search ................ 424/450; 264/4.1, 264/4.3, 4.6

[56] References Cited

U.S. PATENT DOCUMENTS

| | | |
|---|---|---|
| 4,971,802 | 11/1990 | Tarcsay et al. ............... 424/450 |
| 5,123,414 | 6/1992 | Unger ............... 128/654 |
| 5,270,053 | 12/1993 | Schneider et al. ............... 424/450 |

FOREIGN PATENT DOCUMENTS

| | | |
|---|---|---|
| 2145107 | 3/1985 | United Kingdom. |
| 8801864 | 3/1988 | WIPO. |
| 8909593 | 10/1989 | WIPO. |

*Primary Examiner*—Gollamudi S. Kishore
*Attorney, Agent, or Firm*—Gregory D. Ferraro; Karen G. Kaiser; Irving M. Fishman

[57] ABSTRACT

The invention relates to a novel, advantageous process for the preparation of liposomes for the inclusion of water-soluble or hydrophilic substances or mixtures of substances, which process provides the surprising advantage, in comparison with known processes, that the proportion of substances or mixtures of substances actually included is increased and which, when used pharmaceutically, provides the advantage of sterile working conditions. In this process, a mixture consisting of at least one phospholipid and customary lipophilic excipients is subjected to a mobile carrier phase consisting of carbon dioxide and a polar organic solvent (modifier) under supercritical pressure and temperature conditions, the compressed mixed phase is reduced to normal pressure and transferred to an aqueous phase comprising a substance having water-soluble or hydrophilic properties for encapsulation in liposomes.

14 Claims, 1 Drawing Sheet

PROCESS FOR THE PREPARATION OF A LIPOSOME DISPERSION UNDER ELEVATED PRESSURE CONTENTS

This is a CONTINUATION of Ser. No. 08/216,760, filed Mar. 23, 1994 now abandoned.

The present invention relates to a novel, advantageous process for the preparation of a liposome dispersion.

Liposome dispersions comprising various inclusion compounds and phospholipids, such as lecithin, have been described in numerous publications and have already been tested clinically. In order to illustrate the prior art, European Patent Application (hereinafter referred to as EP-A) 178 624 is mentioned, in which there is described a liposome dispersion comprising synthetic, purified sodium 1,2-di(9-cis-octadecenoyl)-3-sn-phosphatidyl S-serine and 1-n-hexadecanoyl-2-(9-cis-octadecenoyl)-3-sn-phosphatidyl choline as phospholipids and lipophilic N-acetyl-D-muramyl-L-alanyl-D-isoglutaminyl-L-alanine-2-(1,2-dipalmitoyl-sn-glycero-3-hydroxyphosphoryloxy)-ethylamide or hydrophilic doxorubicin as encapsulated active ingredients. Those dispersions may be administered intravenously inter alia.

Liposome dispersions comprising inclusion compounds without actual pharmacological properties, such as zinc-phthalocyanine, radioactive labelling compounds or fluorescent compounds, are also known. EP-A-451 103 is mentioned by way of illustration, in which there is described a liposome dispersion comprising zinc-phthalocyanine which, following intravenous administration, may be used in so-called photodynamic chemotherapy only when stimulated with focused light (LASER).

Numerous processes for the preparation of liposome dispersions are described in the literature, for example treatment of an aqueous phospholipid dispersion with ultrasonic waves; dispersion of phospholipids with surfactants in aqueous phase and removal of the surfactants by dialysis; dissolution of phospholipids in organic solvents, removal of the solvent by lyophilisation and dispersion of the residue in aqueous phase; infusion methods or reverse phase evaporation.

Many known preparation processes are disadvantageous since only a fraction of the amount of phospholipids used forms liposomes, and those liposomes likewise comprise only a fraction of inclusion compound. In addition, mixed micelles, gel structures and double-layer aggregates of indefinable size may also be formed. Also known are stability problems, greatly varying liposome size distribution, a lack of reproducibility of the processes themselves, high residual amounts of organic solvents, residual amounts of surfactants, etc.

Furthermore, a common feature of all the preparation processes hitherto known is that only a small proportion of the substance or mixture of substances to be encapsulated is actually encapsulated in the double-layer membrane or in the interior space of the liposomes. The amount of active ingredient that is encapsulated can be increased by selecting a lipophilic substance or mixture of substances. However, if water-soluble or hydrophilic substances are to be encapsulated, the proportion of encapsulated substances always remains low in comparison with the total amount used. Water-soluble or hydrophilic substances are less prone to be enriched from the aqueous phase in a lipid phase. Moreover, lipid membranes have poor stability. When they are leaking, the aqueous contents of the interior space of the liposomes are replaced by the aqueous phase surrounding the liposomes, so that the degree of enrichment of a water-soluble active ingredient in the liposomes is being lowered.

The problem underlying the present invention is to provide a novel, improved process for the preparation of liposomes for the inclusion of water-soluble or hydrophilic substances or mixtures of substances, which process has the surprising advantage in comparison with known processes that the proportion of substances or mixtures of substances actually included is increased and which, when used pharmaceutically, provides the advantage of working conditions that are as sterile as possible.

This problem is solved by the present invention, which relates to an advantageous process for the preparation of a liposome dispersion. The liposome dispersion comprises:

a) a substance for encapsulation in liposomes or a mixture of substances for encapsulation having water-soluble or hydrophilic properties;

b) at least one phospholipid of formula

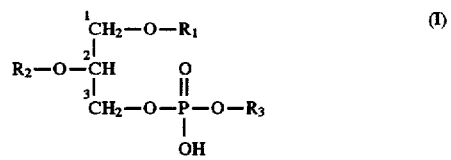

wherein
$R_1$ is $C_{10-20}$acyl,
$R_2$ is hydrogen or $C_{10-20}$acyl, and
$R_3$ is hydrogen, 2-trimethylamino-1-ethyl, 2-amino-1-ethyl, $C_{1-4}$alkyl, $C_{1-5}$alkyl substituted by carboxy, $C_{2-5}$alkyl substituted by hydroxy, $C_{2-5}$alkyl substituted by carboxy and by hydroxy, or $C_{2-5}$alkyl substituted by carboxy and by amino, or salts of those compounds;

c) water in the purity required for the intended application; and, where appropriate, d) additional excipients customary for the intended application.

The process according to the present invention comprises subjecting a mixture consisting of at least one phospholipid b) and, where appropriate, lipophilic excipients d) customary for the intended application, to a mobile carrier phase consisting of carbon dioxide and a polar organic solvent (modifier) under pressure and temperature conditions which are higher than the critical pressure and the critical temperature of a pure carbon dioxide phase, reducing the compressed mixed phase that is obtainable to normal pressure and transferring it to an aqueous phase comprising a substance for encapsulation in liposomes or a mixture of substances for encapsulation a) having water-soluble or hydrophilic properties and, where appropriate, water-soluble excipients d) customary for the intended application, and, where appropriate, removing the organic solvent and/or separating off a fraction of liposomes having a desired diameter range and/or converting the liposome dispersion into a form suitable for the intended application.

In an especially preferred process variant, the phospholipid 1-n-hexadecanoyl-2-(9-cis-octadecenoyl)-3-sn-phosphatidyl choline (POPC) with the lipophilic excipient cholesterol is subjected to a mobile carrier phase consisting of carbon dioxide with approximately from 5 to 7% ethanol as modifier, above the critical pressure and critical temperature of a pure $CO_2$ phase ($\geq 72$ bar, $\geq 32°$ C.). After the compressed mixed phase has been reduced to normal pressure, an aqueous component comprising a water-soluble active ingredient, such as EDATREXATE (10-EDAM), is added thereto, whereupon liposomes comprising a high proportion of that water-soluble inclusion compound form spontaneously.

Within the context of the description of the invention, the terms mentioned hereinbefore and hereinafter are defined as follows:

The expression: A substance for encapsulation in liposomes or a mixture of substances for encapsulation having water-soluble or hydrophilic properties—defines hydrophilic or water-soluble substances and mixtures of substances of the prior art which are known to be capable of inclusion in liposomes having phospholipid double layers.

Liposomes have been described in the literature in numerous publications. Their construction and their use are the subject of many studies. A distinction is made between unilamellar liposomes having one double layer and multilamellar liposomes having several double layers of phospholipids arranged in the manner of an onion skin. The size of the liposomes varies from approximately $1.0 \times 10^{-8}$ to approximately $1.0 \times 10^{-5}$ m.

The therapeutic use of liposomes as carriers especially of lipophilic pharmaceutical active ingredients is known. Liposomes have also been proposed as carriers of other lipophilic substances having biological activity, such as proteins, for example antibodies or enzymes, hormones, vitamins or genes, or, for analytical purposes, as carriers of labelled compounds.

Liposomes and their preparation are described in the synoptical work by Gregoriadis G. (ed.) Liposome Technology, Vol. II, Incorporation of Drugs, Proteins and Genetic Material, CRC Press 1984.

In the case of the substance or mixture of substances for encapsulation in liposomes, a distinction is made between its hydrophilic properties and its water-soluble properties. The hydrophilic property of a substance or mixture of substances is understood as meaning its tendency to build up in the phase interface of water, which is also known in the case of surfactants. This requires the presence of so-called hydrophilic groups in the molecular structure of the substance or mixture of substances in question, which groups are able to interact with water in the sense of attraction.

A substance or mixture of substances is defined as water-soluble when part or all of its weighed amount has dissolved in the aqueous phase and part or all of the substance or mixture of substances in question is present in the solvent water in molecularly disperse distribution. For pharmaceutical purposes, the minimum concentration of dissolved active ingredient in water that is required for the efficacy is sufficient, where appropriate in colloidally disperse distribution; no sedimentation of substances should occur.

Active ingredients that are not readily soluble can be converted into water-soluble pharmaceutically acceptable salts, for example into a hydrobromide, hydrochloride, mesylate, acetate, succinate, lactate, tartrate, fumarate, sulfate, maleate, etc., and rendered usable for the process. Active ingredients that are not readily soluble may also be rendered water-soluble by conversion into water-soluble derivatives or by addition of the solubilisers mentioned below.

Suitable pharmaceutical active ingredients are the following active ingredients in water-soluble form, for example in the form of water-soluble salts, or which have been rendered water-soluble by the addition of solubilisers: antiinflammatory agents, for example dexamethasone, sodium dexamethasone sulfate, hydrocortisone or prednisolone, coronary dilators, for example nifedipine, isosorbitol dinitrate, nitroglycerine, diltiazem, trapidil, dipyridamole or dilazep, prostaglandins, for example prostaglandin $E_j$, $E_2$ or $F_{2\alpha}$, peripheral vasodilators, for example ifenprodil, cinepazet maleate, cyclandelate, cinnarizine or pentoxyphylline, antibiotics, for example ampicillin, amoxycillin, cephalexin, cephradine, cefroxadin, cefaclor, erythromycin, bacampicillin, minocycline or chloramphenicol, antispasmodics, for example propantheline, atropine or scopolamine, antitussives and antiasthmatics, for example theophylline, aminophylline, methylephedrine, procatechol, trimethoquinol, codeine, clofedanolol or dextromethorphan, diuretics, for example furosemide or acetazolamide, muscle relaxants, for example chlorphenesin carbamate, tolperison, eperison or baclofen, mild tranquilisers, for example oxazolam, diazepam, clotiazepam, medazepam, temazepam or fludiazepam, potent tranquilisers, for example sulpiride, clocapramine or zotepin, beta-blockers, for example pindolol, propranolol, carteolol, oxprenolol, metoprolol or labetalol, antiarrhythmics, for example procainamide, disopyramide, ajimalin or quinidine, antigout agents, such as allopurinol, anticoagulants, such as ticlopidine, antiepileptics, for example phenytoin or valproat, antihistamines, for example chlorpheniramine, clemastine, mequitazine, alimemazine, cyproheptadine, agents for treating nausea and dizziness, for example diphenidol, methochlopromide, domperidone or betahistine, antihypertensives, for example reserpine, rescinnamine, methyldopa, prazosin, clonidine or budralazin, sympathomimetics, for example dihydroergotamine, isoproterenol or etilefrin, expectorants, for example bromhexine, carbocisteine, L-ethylcysteine or L-methylcysteine, oral antidiabetics, for example glibenclamide or tolbutamide, cardiovascular agents, for example ubidecarenon or adenosine.

Preferred active ingredients are immunosuppressants, such as cyclosporin, cytostatics, such as EDATREXATE (10-EDAM), doxorubicin, cytarabine, trifosamide, cyclophosphamide, fluorouracil or methotrexate, as well as water-soluble sulfo derivatives of phthalocyanine, for example tetrasulfophthalocyanine, which can be used in photodynamic chemotherapy.

Instead of a pharmaceutical active ingredient or an active ingredient combination, the liposome dispersion may also comprise other substances for encapsulation, such as radioactive labelling compounds or fluorescent compounds.

The nomenclature of the phospholipids (I) and the numbering of the carbon atoms is in accordance with the recommendations made in Eur. J. of Biochem. 79, 11–21 (1977) "Nomenclature of Lipids" by the IUPAC-IUB Commission on Biochemical Nomenclature (CBN) (sn nomenclature, stereospecific numbering).

$R_1$ and $R_2$ as $C_{10-20}$acyl are preferably straight-chained $C_{10-20}$alkanoyl having an even number of carbon atoms and straight-chained $C_{10-20}$alkenoyl having a double bond and an even number of carbon atoms.

$R_1$ and $R_2$ as straight-chained $C_{10-20}$alkanoyl having an even number of carbon atoms are, for example, n-dodecanoyl, n-tetradecanoyl, n-hexadecanoyl or n-octadecanoyl.

$R_1$ and $R_2$ as straight-chained $C_{10-20}$alkenoyl having a double bond and an even number of carbon atoms are, for example, 6-cis-, 6-trans-, 9-cis- or 9-trans-dodecenoyl, -tetradecenoyl, -hexadecenoyl, -octadecenoyl or -icosenoyl, especially 9-cis-octadecenoyl (oleoyl).

A phospholipid (I) wherein $R_3$ is 2-trimethylamino-1-ethyl is referred to by the common name lecithin, and a phospholipid (I) wherein $R_3$ is 2-amino-1-ethyl is referred to by the common name cephalin. There are suitable, for example, naturally occurring cephalin or lecithin, for example cephalin or lecithin from soybeans or chicken eggs, having different or identical acyl groups $R_1$ and $R_2$ or mixtures thereof.

Preference is given to synthetic, substantially pure phospholipids (I) having different or identical acyl groups $R_1$ and $R_2$.

The term "synthetic" phospholipid (I) defines phospholipids which have a defined structure as regards $R_1$ and $R_2$. Such synthetic phospholipids are preferably the lecithins and cephalins defined above, the acyl groups $R_1$ and $R_2$ of which have a specifically defined structure and are derived from a defined fatty acid having a degree of purity greater than approximately 95%. $R_1$ and $R_2$ may be the same or different and unsaturated or saturated. Preferably, $R_1$ is saturated, for example n-hexadecanoyl (=palmitoyl), and $R_2$ is unsaturated, for example 9-cis-octadecenoyl (=oleoyl).

The expression "naturally occurring" phospholipids (I) defines phospholipids which do not have a defined structure as regards $R_1$ and $R_2$. Such natural phospholipids are likewise lecithins and cephalins, the acyl groups $R_1$ and $R_2$ of which are structurally indefinable and are derived from naturally occurring fatty acid mixtures.

The requirement "substantially pure" phospholipid defines a degree of purity of more than 95% (by weight) of the phospholipid (I), which can be demonstrated by suitable methods of determination, for example by paper chromatography.

Special preference is given to synthetic, substantially pure phospholipids (I) wherein $R_1$ is straight-chained $C_{10-20}$alkanoyl having an even number of carbon atoms and $R_2$ is straight-chained $C_{10-20}$alkenoyl having a double bond and an even number of carbon atoms.

In an especially preferred phospholipid (I), $R_1$ is n-dodecanoyl, n-tetradecanoyl, n-hexadecanoyl or n-octadecanoyl and $R_2$ is 9-cis-dodecenoyl, 9-cis-tetradecenoyl, 9-cis-hexadecenoyl, 9-cis-octadecenoyl or 9-cis-icosenoyl.

In such phospholipid (I), $R_3$ as $C_{1-4}$alkyl is, for example, methyl or ethyl.

$R_3$ as $C_{1-5}$alkyl substituted by carboxy, $C_{2-5}$alkyl substituted by hydroxy or $C_{2-5}$alkyl substituted by carboxy or by hydroxy is, for example, 2-hydroxyethyl, 2,3-dihydroxy-n-propyl, carboxymethyl, 1- or 2-carboxyethyl, dicarboxymethyl, 2-carboxy-2-hydroxyethyl or 3-carboxy-2,3-dihydroxy-n-propyl.

$R_3$ as $C_{2-5}$alkyl substituted by carboxy and by amino is, for example, 3-amino-3-carboxy-n-propyl or 2-amino-2-carboxy-n-propyl, preferably 2-amino-2-carboxyethyl. Phospholipids (I) comprising those groups may be in salt form, for example in the form of the sodium or potassium salt.

A very especially preferred phospholipid (I) is synthetic 1-n-hexadecanoyl-2-(9-cis-octadecenoyl)-3-sn-phosphatidyl choline (POPC) having a purity of over 95%.

The names given in parenthesis are also customary for the acyl radicals in the phospholipids (I): 9-cis-dodecenoyl (lauroleoyl), 9-cis-tetradecenoyl (myristoleoyl), 9-cis-hexadecenoyl (palmitoleoyl), 6-cis-octadecenoyl (petroseloyl), 6-trans-octadecenoyl (petroselaldoyl), 9-cis-octadecenoyl (oleoyl), 9-trans-octadecenoyl (elaldoyl), 11-cis-octadecenoyl (vaccenoyl), 9-cis-icosenoyl (gadoleoyl), n-dodecanoyl (lauroyl), n-tetradecanoyl (myristoyl), n-hexadecanoyl (palmitoyl), n-octadecanoyl (stearoyl), n-icosanoyl (arachidoyl).

A salt of the phospholipid (I) is preferably pharmaceutically acceptable. Salts are defined by the existence of salt-forming groups in the substituent $R_3$ and by the free hydroxy group at the phosphorus atom. The formation of internal salts is also possible. Alkali metal salts, especially sodium salts, are preferred.

Component c)—water in the required purity for the intended application—is present in the liposome dispersion in the degree of purity prescribed for the particular use, the water having been rendered germ- and pyrogen-free, for example, in accordance with the provisions of the national pharmacopoeias. For example, water for injection purposes or sterilised water for injection purposes is used.

In addition, the liposome dispersion may comprise further excipients d) that are necessary, for example, for the establishment of isotonic conditions, for example ionic additives, such as sodium chloride, or non-ionic additives (structure formers), such as sorbitol, mannitol or glucose, or water-soluble stabilisers for the liposome dispersion, such as lactose, fructose or sucrose. In particular, the liposome dispersion comprises those additives, for example sodium chloride or mannitol, in the prescribed amounts necessary for the establishment of isotonic conditions in the injection solutions. In an especially preferred embodiment of the process, the liposome dispersion is prepared with the lipophilic excipient cholesterol. That excipient is added with the mentioned phospholipids to the mobile carrier phase consisting of $CO_2$ and the modifier ethanol. When that mixed phase is reduced to normal pressure, liposomes form in the aqueous phase and wherein the excipient cholesterol is incorporated in the double layers consisting of phospholipids. Liposomes having cholesterol in the double layer are distinguished by increased stability.

In addition to the water-soluble excipients, the liposome dispersion may comprise further excipients that can be used for liquid pharmaceutical formulations, which excipients increase the water-solubility of the mentioned active ingredients, for example emulsifiers, wetting agents or surfactants, especially emulsifiers such as oleic acid, non-ionic surfacants of the fatty acid polyhydroxy alcohol ester type, such as sorbitan monolaurate, monooleate, monostearate or monopalmitate, sorbitan tristearate or trioleate, polyoxyethylene adducts of fatty acid polyhydroxy alcohol esters, such as polyoxyethylene sorbitan monolaurate, monooleate, monostearate, monopalmitate, tristearate or trioleate, polyethylene glycol fatty acid esters, such as polyoxyethyl stearate, polyethyleneglycol400 stearate, polyethylene glycol 2000 stearate, especially ethylene oxide/propylene oxide block polymers of the Pluronic® type (Wyandotte Chem. Corp.) or the Synperonic® type (ICI).

The advantage of the process is that a large amount of a water-soluble substance, especially of a water-soluble pharmaceutical active ingredient, such as EDATREXATE (10-EDAM), doxorubicin, cytarabine or trifosamide, can be encapsulated in liposomes. The preparation processes hitherto known are disadvantageous for water-soluble inclusion compounds since only small amounts are encapsulated in liposomes, while most of the compound remains in solution in the aqueous phase.

There are used as phospholipid preferably the above-mentioned natural or synthetic, substantially pure derivatives of lecithin, especially 1-n-hexadecanoyl-2-(9-cis-octadecenoyl)-3-sn-phosphatidyl choline (POPC). Cholesterol is preferably used as the customary lipophilic excipient. The incorporation of that excipient, which is also present in stable, natural membranes, yields liposomes having an especially stable structure, which remain stable to storage for up to several months.

The expression "mobile carrier phase consisting of carbon dioxide and a polar organic solvent (modifier)" defines a mixed phase consisting of carbon dioxide and polar solvent under pressure and temperature conditions which are in the range of or above the critical point of that mixed phase. The pressure and temperature conditions to be applied are higher than the critical pressure and the critical temperature of a pure carbon dioxide phase (72 bar and 32° C.). There is used as polar organic solvent (modifier) preferably ethanol, but also methanol, tert-butanol, isopropanol, n-propanol, methyl isobutyl ketone, acetone, etc.

The pressure in the mobile carrier phase consisting of carbon dioxide and the modifier, preferably ethanol, is increased to a value of at least 72 bar in a closed apparatus, see FIG. 1. Preferred are values in the supercritical range of a pure $CO_2$ phase of up to approximately 1000 bar, preferably up to approximately 400 bar, especially from 200 to 300 bar. Preferred working temperatures are temperatures from above room temperature to approximately 100° C., preferably from 50° to 60° C. The minimum supercritical conditions for a pure $CO_2$ phase are approximately 72 bar and 32° C. (slightly varying figures are given in physicochemical tables on account of differing measuring methods).

The expression "compressed mixed phase" defines a homogeneous mixture under supercritical or close to critical pressure and temperature conditions and is consisting of the mobile carrier phase, the phospholipid b) and, where appropriate, lipophilic excipients d) customary for the intended application, especially cholesterol.

The size of the liposomes formed in the aqueous phase is dependent upon various conditions, for example the composition of the mobile carrier phase, the amount of active ingredient and the lipid components, the mixing ratio thereof and the concentration in the aqueous dispersion, selection of pressure and temperature conditions, the rate of flow or variation in mixer types or capillary geometry, for example the length and diameter of the depressurisation capillary in the apparatus used for the process.

The removal of the organic solvent (modifier), which may be necessary for pharmaceutical applications, may be carried out by various methods, for example evaporation, dialysis or gel filtration/gel chromatography. Ethanol may be removed from the aqueous solution by gel filtration (Sephadex® G 50). Ethanol is preferably removed with $CO_2$ using the counterflow principle with the application of supercritical pressure and temperature conditions in accordance with the process described in U.S. Pat. No. 4,492,808.

Aqueous dispersions having an acidic reaction are preferably buffered to pH 7.0 to 7.8, preferably 7.2 to 7.4. Pharmaceutically acceptable buffer solutions are preferably used for that purpose, the preparation of which is described in various national pharmacopoeias, for example the European, U.S., German or British Pharmacopoeia. The dispersion may be neutralised also by the addition of a pharmaceutically acceptable, dilute aqueous base, for example dilute aqueous sodium hydroxide solution. Neutralisation is customarily carried out with simultaneous pH monitoring. Where necessary, the dispersion is made up with sterile, germ-free and pyrogen-free water.

It is possible to obtain an especially uniform size distribution of the liposomes by after-treatment of the liposome dispersion, for example by treatment with ultrasonic waves or extrusion through straight-pored filters (e.g. Nucleopore®).

The separation and isolation of a fraction of large liposomes from a fraction containing small liposomes, insofar as it is at all necessary, is likewise effected by means of conventional separation methods, for example gel filtration or ultrafiltration, for example with Sepharose® 4B or Sephacryl® (Pharmacia SE) as carrier, or by sedimentation of the liposomes in an ultracentrifuge, for example with a gravitational field of 160,000×g. For example, after centrifugation for several hours, for example about 3 hours, in that gravitational field, liposomes are deposited, whereas small liposomes remain in dispersion and can be decanted. Repeated centrifugation results in complete separation of the large liposomes from the small liposomes.

Gel filtration especially can be used to separate off all the liposomes present in the aqueous phase having a diameter of more than about $6.0 \times 10^{-8}$ m and also non-encapsulated components and excess, dispersed lipids that are present in high molecular weight aggregates and thus to produce an aqueous dispersion having a fraction of liposomes of relatively uniform size.

The completed formation of liposomes and their size distribution in the aqueous phase can be demonstrated in a manner known per se by various physical measuring methods, for example with freeze fracture samples and thin sections under an electron microscope or by X-ray diffraction, by dynamic light scattering, by mass determination of the filtrate in an analytical ultracentrifuge and especially by spectroscopy, for example in the nuclear magnetic resonance spectrum ($^1$H, $^{13}$C and $^{31}$P).

The liposome dispersion may be administered directly after removal of organic solvents, or it may be converted by freeze-drying into a lyophilisate, which is reconstituted immediately before administration by the addition of water in the required injection volume.

FIG. I depicts the closed apparatus in which the instant invention may be carried out.

The process itself is carried out in a closed apparatus, which is illustrated in greater detail in FIG. 1. The components of the apparatus are as follows, the numbering of the components corresponding to the reference numerals in the drawing:

| | | |
|---|---|---|
| 1 | $CO_2$ reservoir | Pure (99.9%) $CO_2$ from tank with immersed pipe (Carbagas CH-Basel). |
| 2 | $CO_2$ pump | Gilson 306 (Synmedic AG, CH-Zürich) with MGW Lauda RM6 refrigerating unit, IG instrumentengesellschaft AG CH-Zürich. |
| 3 | Pump pressure safety device | Gilson 805S (Synmedic). |
| 4 | Pulse damper | Reduces vibrations of the pump. Approx. 2 m 1/8 capillary in diameter (Supelco SA, CH-Gland). |
| 5 | Waste vessel | For solvent residues. |
| 6 | Modifier reservoir | (Modifier) with ethanol. |
| 7 | Modifier pump with | Gilson 305 (Synmedic). |
| 8 | Pressure safety device for pump | incorporated in Gilson 305. |
| 9 | Static mixer | Lee Visco Mixer, Lee TCMA 2520113T 648430, 2 units, Lee Hydraulische Miniaturkomponenten D-Frankfurt. |
| 10 | Dynamic mixer | Gilson 811B (Synmedic). |
| 11 | Filter | SSI 05-0150 (Supelco). |
| 12 | Injector | Gilson 231 and Gilson Dilutor 401 (Synmedic). |
| 13 | Check valve | Spectra-Physics check valve with sleeve (Ciba-Geigy, CH-Basle). (Spectra Physics, CH-Allschwil). |
| 14 | Pressure safety valve | No.20631 25, 2500-25000 Psig (Haskel Inc. Burbank Ca., USA). |
| 15 | Cross piece | Valco (Supelco SA, rebored to approx. 0.5 mm diameter). |
| 16 | Manometer | 0-600 bar (IKA, D-Staufen) for recycling system I. |
| 17 | Recycling pump | Gilson 303 (Synmedic, heating sleeve, Ciba-Geigy). |
| 18 | UV detector | Linear UVIS 200 with SFC cell and heating tube, |

-continued

| | | |
|---|---|---|
| | | 1.4 µl cell volume, 2 mm path length (Henngeler, CH-Riehen). |
| 19 | Extraction cell | Steel tube with threaded connectors. |
| 20 | Static mixer | 1–3 mixing elements (SMXE DN 3.2) (Sulzer Chemtech, CH-Winterthur) Steel tube with threaded connector (Ciba-Geigy). |
| 21 | Pressure sensor | Piezoresis five series 15 type PA-15 (Keller AG, CH-Winterthur) Connection with minimum dead volume (Ciba-Geigy). |
| 22 | Pressure regulator | Piezo pressure regulator with piezo crystal and heating element (EP-A-0 427 671). |
| 23 | Piezo driver | P-864 and PZT-control E-808. (Polyscience AG, CH-Cham). |
| 24a/24b | T-piece | SSI 01-0165 (Supelco), 24b preferred rebored to 0.5 mm diameter. |
| 25 | Static mixer | 1 rod with 5 pieces (SMV-2 DN 10, Sulzer Chemtech, CH-Winterthur Steel tube with threaded connector (Ciba-Geigy). |
| 26 | Collecting vessel | Three-necked round flask (50 ml) |
| 27 | Recycling pump | Tube constriction pump Kontron Analytic LC-Pump Kontron Inst. AG, CH-Zürich |
| 28 | Water bath | with heating unit |
| 29 | T-piece | as 24 |
| 30a/30b | Check valve | as 13, 30b preferred |
| 31a/31b | Metering pump | for water-soluble substance as 7, 31b preferred |
| 32a/32b | Vessel | Supply of water-soluble substance, 32b preferred |
| 33 | Static mixer | as 20 |
| A,C,D,F,G,I,J,L,N | | Three-way taps SSI 02-0124 (Supelco). |
| B,E,H,K,M,O | | Two-way taps SSI 02-0120 (Supelco). |

The pumps 2 and 7 convey the $CO_2$ and the modifier from the reservoirs 1 and 6 into the apparatus. The $CO_2$ pump is preferably cooled to $-10°$ C., the $CO_2$ having a density of approximately 1 g/ml and being easy to pump. The pump pressure safety device 3 displays the pressure of the pumps 2 and 7. The pulse damper 4 damps the pressure pulses of the pumps 2 and 7, which occur when the pump piston is retracted. The pump control 8 controls the flow and the phase mixing ratio of the two pumps 2 and 7. The static mixers 9, 20, 25, 33 have no movable parts. Mixing occurs as a result of currents in a steel tube in which several mixing elements (current breakers) are incorporated, which splits and collects the current lines. The dynamic mixer 10 has a movable part. The movement produces a turbulent current, which mixes the phases introduced. The filter 11 retains undesired foreign particles in the mobile carrier phase consisting of $CO_2$ and modifier. The injector 12 is provided for further additions of modifier. The check valve 13 allows the mobile carrier phase to pass only in the direction A→B. Should the pressure in direction B fall and become less than the pressure in direction A, compressed phase is introduced until stable, equal pressure conditions prevail. The adjustable pressure safety valve 14 opens in the case of undesired overpressure. The cross piece 15 is open in all directions. The manometer 16 displays the pressure in the recycling circuit I, which is defined by the arrangement C-D-19-20-F-G-18-17-15-C, or, preferably, C-15-17-18-G-F-20-D-C. In the recycling circuit I, the compressed homogeneous mixed phase is under homogeneous conditions. The recycling pump 17 conveys the mobile carrier phase consisting of $CO_2$ and modifier through the extraction cell 19 and the static mixer 20 in the recycling circuit I, whereupon the lipophilic constituents (phospholipid and, where appropriate, cholesterol) previously introduced into the extraction cell 19 are dissolved. The UV detector 18 displays the degree of homogenisation of the compressed lipid-containing mixed phase with the lipophilic constituents introduced into the extraction cell 19. The detector signal is recorded on a plotter. The extraction cell 19 is a pressure-stable steel tube with threaded connectors and filters at the inlet and outlet. Emptied chromatographic columns may also be used for that purpose. The pressure sensor 21 measures the pressure downstream of the recycling circuit I. The pressure regulator 22 comprises a piezo crystal, which is controlled by the piezo driver 23 and thus establishes the required pressure conditions. The piezo driver 23 automatically establishes the required pressure independently of the flow conditions. In the arrangement 24a,b-30a,b-31a,b-32a,b water soluble or hydrophilic substance may be added to the system which are to be encapsulated in liposomes. The arrangement 24b-30b-31b-32b in the low pressure range is preferred. The addition in arrangement 24a-30a-31a-32a is also possible. The static mixer 25 serves as a homogeniser in the formation of liposomes. The recycling pump 27 conveys the aqueous phase from the collecting vessel 26 through the static mixer 33 into the recycling circuit II, which is defined by the arrangement 29-34-26-27-29. In that circuit, uncontrolled foam formation on depressurisation of the mixed phase is prevented and homogeneity of the depressurised mixed phase is established. The water bath 28 ensures that temperature conditions in the recycling circuit I, in the pump head of the recycling pump 17 and in the detection cell 18 are constant. The three-way taps A,C,D,F, G,I,J,L,N allow the currents of the compressed phase to pass through (one outer always open) or distribute them in two directions (two outlets open). The two-way taps B,E,H,K, M,O allow the currents to flow through or prevent them from passing.

The process that can be carried out in the closed apparatus according to FIG. 1 and the product currents can be described using a representative phospholipid and a representative lipophilic excipient (cholesterol) by means of the following partial steps:

α) The closed apparatus described above and in FIG. 1 is charged with a mixed phase of $CO_2$/ethanol (=mobile carrier phase) (pressure regulator: 250 bar, pressure regulator temperature: 90° C., water bath temperature: 60° C., adjustment at components 21 and 28). Taps D,F,J,L and N are closed. Taps A,B,C,E,G,H,I,K,M and O are open. The mobile phase flows through the apparatus in direction A,B,C,D,E,F,G,H,I,21,G,18,17, 15,C or, in the alternative, A,B,C,D,15,17,18,G,H,I,21, and through the bypass A,I, but not through the extraction cell 19. The pressure is adjusted to 250 bar using the pressure regulator 22. The flow rate of the metering pump 31 is dependent from the concentration of lipids in the drepressurised mixed phase.

β) The phospholipid, for example POPC, and the cholesterol are weighed out into an extraction cell (molar ratio 7:3). The extraction cell is inserted at 19 and all components downstream of A and upstream before 21 are kept at a constant temperature of 54° C. The taps are set in the same directions as in process step α).

γ) Measurement of the homogeneity of the mobile carrier phase at the detector 18. The UV absorption curve is recorded using a plotter.

δ) Taps D and F are opened and taps E and H are closed. All other taps remain in the same positions as in process step α). The recycling circuit I: C,D,19,20,F,G,18,17, 15,C or, in the alternative, C,15,17,18,G,F,20,19,D,C, is thus closed. The check valve 13 maintains continuous pressure in the recycling circuit I. Pressure equalisation with pumps 2 and 7 via bypass A-I and pressure regulator 22.

ε) The phospholipid weighed out with cholesterol in the extraction cell 19 dissolves until equilibrium is reached in the compressed mixed phase.

ζ) When stable equilibrium has been reached (UV absorption stable 18), taps A,I,D and F are closed. Taps E and H are opened and the pump 31 is working. The remaining taps are set in the same directions as in process step α).

η) The compressed mixed phase comprising phospholipids and cholesterol is decompressed out of the recycling circuit I through the pressure regulator 22. The mixed phase is released from 24b into the aqueous phase containing the hydrophilic or water soluble substance, whereupon liposomes form spontaneously.

ν) The aqueous liposome dispersion is diluted and homogenised in the recycling circuit II consisting of the arrangement 29-34-26-27-29.

ι) When the UV absorption has reached the original level of the mobile carrier phase (no noticeable absorption for phospholipids) and corresponds to the absorption in process step γ), the experiment is concluded and the liposome suspension is analysed qualitatively and quantitatively by HPLC. A portion of the suspension is examined under a light-optical microscope.

EXAMPLE 1

Placebo test with the phospholipid [1-n-hexadecanoyl-2-(9-cis-octadecenoyl)-3-sn-phosphatidyl choline (POPC)] and cholesterol. The test is carried out according to steps α)-ι) and the apparatus shown in FIG. 1, but without using the recycling circuit II. The components mentioned above correspond to the reference numerals in FIG. 1, which are described above.

Weighed amount:
52.86 mg of POPC
8.97 mg of cholesterol.
Mobile carrier phase:
$CO_2$ and ethanol (96% v/v).
Detection:
UV absorption at 210 nm.
$CO_2$ flow:
0.465 ml/min. at pump 2.
Modifier 0.035 ml/min. at pump 7.
Pressure:
Upstream of extraction cell at components 8 and 16: approx. 300 bar.
Downstream of extraction cell at component 22: approx. 250 bar
Pressure variations of approx. 10 bar occur (after retraction of the pump piston) owing to the use of a recycling pump (piston pump—comp. 17).
Temperature:
Water bath: 54° C. (comp. 28).
Detection cell: approx. 54° C. (comp. 18).
Recycling pump head: approx. 54° C. (comp. 17).
Pressure regulator heated to 90° C.
Extraction cell:
Valco type (precolumn) with a volume of 350 µl.
Analysis by means of HPLC shows no decomposition products in the liposome suspension. POPC and cholesterol are not being denatured during the liposome formation process. The following mounts were found in the liposome dispersion that is obtainable:

POPC
29.5 mg (55.8% yield)
Cholesterol
6.2 mg (69.4% yield)
molar ratio POPC:cholesterol=3:1.

EXAMPLE 2

This example test is carried out according to steps α)-ι) and the apparatus shown in FIG. 1, with the inclusion of the recycling circuit II and the addition of lipophilic or water soluble substance. The components mentioned correspond to the reference numerals in FIG. 1, which are described above:

Weighed amount:
12.20 mg of cholesterol USP XX
59.40 mg of POPC
molar ratio of POPC to cholesterol: 2.5:1
0.425 mg/ml of zinc-phthalocyanine tetrasulfonate [$ZnPc(SO_3H)_4$] in dest. water
$CO_2$ flow:
1.86 ml/min. at pump 2
0.14 ml/min. at pump 7
Flow rate:
at metering pump 31
0.00–5.59 min.
12.0 µl/min.
6.00–10.59 min.
4.5 µl/min
11.00–17.00 min.
1.5 µl/min.

The process is carried out analogously to Example 1 under the conditions described therein. Analysis by means of HPLC shows no decomposition products in the liposome dispersion. POPC, cholesterol and zinc-phthalocyanine tetrasulfonate are not denatured during the liposome formation process. Before gel filtration, the following amounts were found in the liposome dispersion that is obtainable:

POPC:
45.70 mg (77% of the weighed amount)
Cholesterol:
8.14 mg (67.0% of the weighed amount)
molar ratio POPC:cholesterol=3:1.

1.0 ml of liposome dispersion (1.03 mg of cholesterol and 5.78 mg of POPC) are gel-filtered in order to remove $ZnPc(SO_3H)_4$ that has not been included. The following mounts are found in the fractions with liposomes:

POPC:
4.84 mg (84% of the weighed amount)
Cholesterol:
0.90 mg (87% of the weighed amount)
$ZnPc(SO_3H)_4$
3.6 µg, of which 2.6 µg in liposomes.
72% active ingredient included with an inclusion volume of approx. 0.7 l/mol lipid.

What is claimed is:

1. A process for the preparation of a liposome dispersion comprising subjecting at least one phospholipid of the formula

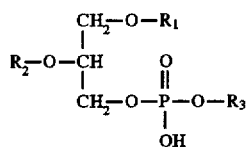

wherein

R₁ is $C_{10-20}$acyl,

R₂ is hydrogen or $C_{10-20}$acyl, and

R₃ is hydrogen, 2-trimethylamino-1-ethyl, 2-amino-1-ethyl, $C_{1-4}$alkyl, $C_{1-5}$alkyl substituted by carboxy, $C_{2-5}$alkyl substituted by hydroxy, $C_{2-5}$alkyl substituted by carboxy and by hydroxy, or $C_{2-5}$alkyl substituted by carboxy and by amino, or a salt of such phospholipid to a mobile carrier phase consisting of carbon dioxide and a polar organic solvent under pressure and temperature conditions which are higher than the critical pressure and the critical temperature of a pure carbon dioxide phase, reducing the compressed mixed phase that is obtainable to normal pressure and transferring it to an aqueous phase comprising water in the purity required for the intended application and a non-proteinaceous substance or a mixture of non-proteinaceous substances having water-soluble or hydrophilic properties for encapsulation in liposomes and removing the organic solvent and/or separating off a fraction of liposomes having a desired diameter range and/or converting the liposome dispersion into a form suitable for the intended application.

2. A process according to claim 1, where the non-proteinaceous substance or mixture of substances for encapsulation is at least one compound selected from the group consisting of a radioactive labelling compound, and a pharmaceutical active ingredient.

3. A process according to claim 2, wherein hydrophilic or water-soluble pharmaceutical active ingredients are used as the non-proteinaceous substance a) for encapsulation.

4. A process according to claim 2, wherein zinc-phthalocyanine tetrasulfonate [ZnPc(SO₃H)₄] is used as the non-proteinaceous substance a) for encapsulation.

5. A process according to claim 1, wherein synthetic, substantially pure 1-n-hexa-decanoyl-2-(9-cis-octadecenoyl)-3-sn-phosphatidyl choline is used as the phospholipid b).

6. A process according to claim 1, wherein sterilized water for injection purposes is used as component c).

7. A process according to claim 1, wherein the liposome composition further comprises cholesterol.

8. A process according to claim 1, wherein the liposome composition further comprises at least one water-soluble excipient for the establishment of isotonic conditions.

9. A process according to claim 1, wherein the polar organic solvent is ethanol.

10. A process according to claim 1, wherein a pressure range of approximately from 72 to 400 bar is used.

11. A process according to claim 10, wherein a pressure range of approximately from 200 to 300 bar is used.

12. A process according to claim 1, wherein an elevated temperature of approximately from 32° to 100° C. is used.

13. A process according to claim 12, wherein an elevated temperature of approximately from 50° to 60° C. is used.

14. A process according to claim 1, wherein the liposome dispersion that is obtainable is convened into a lyophilisate which is then reconstituted by the addition of water in the required injection volume.

* * * * *